United States Patent [19]

Eakin et al.

[11] 4,025,647

[45] May 24, 1977

[54] SALICYLANILIDE DERIVATIVES HAVING ANTHELMINTIC ACTIVITY

[75] Inventors: Murdoch Allan Eakin; Justus Kenneth Landquist, both of Macclesfield, England

[73] Assignee: Imperial Chemical Industries Limited, London, England

[22] Filed: Sept. 15, 1975

[21] Appl. No.: 613,559

[30] Foreign Application Priority Data

Sept. 20, 1974 United Kingdom ............ 41053/74

[52] U.S. Cl. .............................. 424/304; 260/207; 260/207.1; 260/465 D; 260/480; 260/559 S; 260/559 T; 424/226; 424/324; 424/311
[51] Int. Cl.$^2$ ............. A61K 31/275; C07C 121/80
[58] Field of Search ............... 260/465 D; 424/304

[56] References Cited

UNITED STATES PATENTS

| 3,325,353 | 6/1967 | Early et al. .................. 260/465 X |
| 3,798,258 | 3/1974 | Patchett et al. ............... 260/465 X |
| 3,839,443 | 10/1974 | Meek ........................... 260/465 X |

OTHER PUBLICATIONS

Monsanto Co., Chemical Abstracts, vol. 68, 49315z (1968).

*Primary Examiner*—Dolph H. Torrence
*Attorney, Agent, or Firm*—Cushman, Darby & Cushman

[57] ABSTRACT

Salicylanilide derivatives bearing a 3-secondary or tertiary alkyl, 5-cyano, alkanoyl, phenylazo, phenylthio, phenylsulphinyl or phenylsulphonyl, an optional 6-methyl and a variety of substituents on the anilino ring. The compounds have anthelmintic activity especially against liver fluke.

7 Claims, No Drawings

SALICYLANILIDE DERIVATIVES HAVING ANTHELMINTIC ACTIVITY

This invention relates to new amides and in particular it relates to novel salicylanilide derivatives which possess anthelmintic activity.

According to the invention there is provided a salicyanilide ddrivative of the formula:-

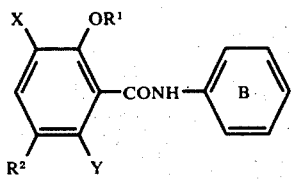

wherein $R_1$ is a hydrogen atom or an alkanoyl radical of from 1 to 4 carbon atoms; $R_2$ is a cyano radical, an alkanoyl radical of from 1 to 4 carbon atoms, or a phenylazo radical of the formula:-

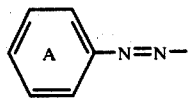

or a phenylthio, phenylsulphinyl or phenylsulphonyl radical of the formula:-

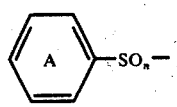

wherein $n$ is zero or the integer 1 or 2, and ring A optionally bears from 1 to 3 substituents selected from halogen atoms, cyano, nitro and trifluoromethyl radicals and alkyl and alkoxy radicals of from 1 to 4 carbon atoms; X is a secondary or tertiary alkyl radical of from 3 to 6 carbon atoms; Y is a hydrogen atom or a methyl radical; and ring B bears from 1 to 3 substituents selected from halogen atoms, cyano, nitro and trifluoromethyl radicals, alkyl radicals of from 1 to 4 carbon atoms, and phenoxy, phenylthio, phenylsulphinyl, phenylsulphonyl and benzoyl radicals each optionally bearing one or two substituents selected from halogen atoms and cyano and nitro radicals; or a base-addition salt thereof.

A particularly suitable value for $R^1$ when it is an alkanoyl radical is, for example, an acetyl radical.

A particularly suitable value for $R^2$ when it is an alkanoyl radical is, for example, a formyl or acetyl radical.

A particularly suitable value for X when it is a secondary alkyl radical is, for example, an isopropyl radical, and a particularly suitable value when it is a tertiary alkyl radical is, for example, a t-butyl, t-pentyl, 1,1-dimethylbutyl or 1-ethyl-1-methylpropyl radical.

A particularly suitable value for an alkyl radical when it is a substituent on ring A is, for example, a methyl radical.

A particularly suitable value for an alkoxy radical when it is a substituent on ring A is, for example, a methoxy radical.

A particularly suitable value for a halogen atom when it is a substituent on ring A is, for example, a chlorine or bromine atom.

A particularly suitable value for an alkyl radical when it is a substituent on ring B is, for example, a methyl or isopropyl radical.

A particularly suitable value for a halogen atom when it is a substituent on ring B is, for example, a chlorine, bromine or iodine atom.

A particularly suitable value for a substituent on ring B when that substituent is a substituted phenoxy, phenylthio, phenylsulphinyl, phenylsulphonyl and benzoyl radical is such a radical bearing a halogen atom, for example, a fluorine, chlorine or bromine atom and, in the case where the ring B substituent is a substituted phenoxy or phenylthio radical, is such a radical bearing a cyano or nitro radical in addition to, or in place of, the halogen substituent.

A particular group of salicylanilide derivatives of the invention comprises those compounds of the formula I wherein $R^1$ is a hydrogen atom, X is a t-butyl radical and Y is a methyl radical. Within this group, other particular groups of salicylanilides of the invention comprise those compounds of formula I wherein:- a. $R^2$ is a cyano radical,
b. $R^2$ is a phenylazo radical,
c. $R^2$ is a phenylthio radical,
d. $R^2$ is a phenylsulphonyl radical,
e. ring B forms a phenyl radical bearing substituents in the 2- and 4-positions as stated above, for example a phenyl radical bearing a halogen atom or a trifluoromethyl radical at the 2-position and a nitro or cyano radical at the 4-position, especially a 2-chloro-4-nitro-, 2-trifluoromethyl-4-nitro- and a 2-trifluoromethyl-4-cyanophenyl radical,
f. ring B forms a phenyl radical bearing substituents in the 3- and 4-positions, or 3-,4- and 5-positions, at least one of which substituents is a cyano radical or a halogen atom and the remaining substituent or substituents are as stated above,
g. ring B bears a 4-phenylsulphonyl radical,
h. ring B bears a 4-phenylthio radical, and
i. ring B bears a 4-phenoxy radical; and wherein in each of groups (b) to (d) the phenyl radical (ring A) is optionally substituted as stated above; and wherein in each of groups (g) to (i) the phenylsulphonyl, phenylthio and phenoxy radical is optionally substituted as stated above and ring B optionally bears one or two additional substituents as stated above.

Yet further particular groups of salicylanilides of the invention comprise those compounds of the formula I wherein $R^2$ has one of the values set out above in groups (a) to (d) and ring B has one of the values set out above in groups (e) to (i).

Yet further particular groups of salicylanilide derivatives of the invention comprise the 2-O-acetyl derivatives of the compounds of the formula I within any of the particular groups set out above.

A particularly suitable base addition salt is, for example, an alkali metal or alkaline earth metal salt, for example the sodium, potassium, calcium or magnesium salt, or a salt with an organic base, for example the piperidine, piperazine or trimethylamine salt.

Specific salicylanilide derivatives are those hereinafter described in the Examples, and of these a preferred salicylanilide derivative of the invention is, for example, 2',4'-dichloro-5-cyano-3-t-butyl-6-methyl-salicylanilide, 2'-trifluoromethyl-4',5-dicyano-3-t- butyl-6-methylsalicylanilide, 2'-trifluoromethyl-4'-(4-cyanophenylthio)-5-cyano-3-t-butyl-6-methylsalicylanilide, 2'-bromo-4'-(4-cyanophenylthio)-5-cyano-3-t-butyl-6-methylsalicylanilide, 2'-trifluoromethyl-4'-(4-bromophenylsulphonyl)-5-cyano-3-t-butyl-6-methylsalicylanilide, 2'-trifluoromethyl-4'-(4-chlorophenylsulphonyl)-5-cyano-3-t-butyl-6-methylsalicylanilide, 2'-trifluoromethyl-4'-nitro-5-(4-nitrophenylthio)- 3-t-butyl-6-methylsalicylanilide, 2'-chloro-4'-nitro-5-(4-nitrophenylthio)-3-t-butyl-6-methylsalicylanilide, 2'-chloro-4'-nitro-5-(4-nitrophenylsulphonyl)-3-t-butyl-6-methylsalicylanilide, 2'-trifluoromethyl-4'-bromo-5-(4-nitrophenylsulphonyl)-3-t-butyl-6-methylsalicylanilide, 2'-chloro-4'-nitro-5-(2-nitro-4-chlorophenylsulphonyl)-3-t-butyl-6-methylsalicylanilide, 2'-methyl-4'-nitro-5-(4-cyanophenylazo)-3-t-butyl-6-methylsalicylanilide, 3'-chloro-4',5-dicyano-3-t-butyl-6-methylsalicylanilide, 4'-chloro-3',5-dicyano-3-t-butyl-6-methylsalicylanilide or 2'-bromo-4',5-dicyano-3-t-butyl-6-methylsalicylanilide, or a base addition salt thereof.

The salicylanilide derivatives of the invention may be obtained by any process applicable to the manufacture of analogous compounds. Such processes are exemplified by the following in which $R^1$, $R^2$, X, Y, A, B and $n$ have the meanings stated above unless specifically stated otherwise:- a. Forming an amide by reacting a salicylic acid derivative of the formula:-

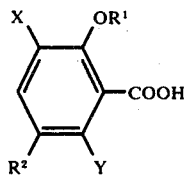

or a reactive ester or mixed anhydride thereof with an aniline derivative of the formula:-

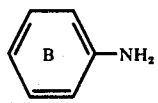

Thus, for example, a salicylic acid derivative of the formula II as set out above, may conveniently be reacted with an aniline derivative of the formula III as set out above, in the presence of a condensing agent, for example, phosphorous trichloride. This reaction is conveniently carried out by heating the reactants together, for example, at a temperature of from 50° C. to 250° C. in an inert solvent of boiling point from 100° C. to 250° C., for example, chlorobenzene or 1,2,4-trichlorobenzene.

b. For a salicylanilide derivative of formula I wherein $R^2$ is a cyano radical, and/or ring B bears a cyano radical, reacting the corresponding salicylanilide derivative of the formula I wherein $R^2$ is a displaceable substituent, for example a halogen atom, and/or ring B bears a displaceable substituent, for example a halogen atom, with cuprous cyanide.

The reaction is conveniently carried out by heating the reactants together in an inert solvent, for example, dimethylformamide, at a temperature of, for example, from 100° C. to 200° C.

A particularly suitable displaceable substituent when it is a halogen atom is, for example, a bromine or iodine atom.

c. For a salicylanilide derivative of formula I wherein $R^2$ is a formyl radical, formylating the corresponding salicylanilide derivative of formula I wherein $R^2$ is a hydrogen atom by reaction with, for example, hexamethylene tetramine or dichloromethyl methyl ether, each in the presence of an acid catalyst.

A particularly suitable acid catalyst in the case of hexamethylene tetramine is, for example, trifluoroacetic acid. A particularly suitable catalyst in the case of dichloromethyl methyl ether is for example, a Lewis acid, for example, titanium tetrachloride.

The reaction with hexamethylene tetramine is conveniently carried out in an excess of acid catalyst as solvent, for example, trifluoroacetic acid, and at a temperature of from 50° C. to 150° C., and preferably at from 70° C. and 100° C.

d. For a salicylanilide of the formula I wherein $R^2$ is a radical of the formula:-

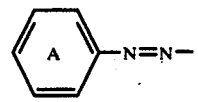

reacting the corresponding salicylanilide derivative of the formula I wherein $R^2$ is a hydrogen atom with a diazonium salt of the formula:-

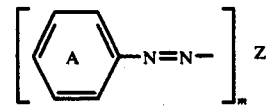

wherein Z is the anion derived from an inorganic acid of the formula $H_mZ$ and $m$ is the integer 1,2 or 3.

A particularly suitable anion Z is, for example, the chloride, sulphate or phosphate anion, wherein $m$ has the value 1,2 or 3 respectively.

The reaction is conveniently carried out at a temperature of from 0° C. to 25° C. and in the presence of a polar solvent, for example, water or ethanol, or in a mixture of these solvents. The reaction is preferably carried out under basic conditions, for example, in the presence of sodium ethoxide or sodium hydroxide, and at a temperature of from 0° C. to 20° C.

e. For a salicylanilide derivative of formula I wherein $R^2$ is a radical of the formula:-

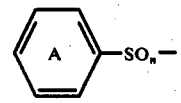

wherein $n$ is the integer 1 or 2, and/or wherein ring B bears an optionally substituted phenylsulphinyl or phenylsulphonyl radical, oxidising the corresponding salicylanilide derivative of formula I wherein $R^2$ is a radical of the formula:-

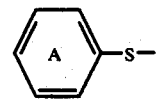

and/or where ring B bears an optionally substituted phenylthio substitutent respectively.

The oxidation is conveniently carried out by using, for example, hydrogen peroxide as the oxidising agent and by heating the reactants at from 20° C. to 150° C. The oxidation is conveniently carried out in a polar organic solvent, for example, acetic acid.

When it is desired to obtain a salicylanilide derivative of the formula I wherein $R^2$ is a radical of the formula:-

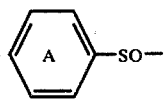

or wherein ring B bears an optionally substituted phenylsulphinyl substituent, the oxidation is preferably carried out at a temperature of from 20° C. to 100° C., for example, from 50° C. to 100° C. and preferably using a molecular equivalent or a slight excess of oxidising agent.

When it is desired to obtain a salicylanilide derivative of the formula I wherein $R^2$ is a radical of the formula:-

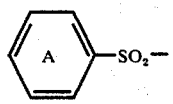

or wherein ring B bears an optionally substituted phenylsulphonyl substituent, the oxidation is preferably carried out at a temperature of from 80° C. to 150° C., for example at from 95° C. to 120° C. and preferably using a large excess of oxidising agent.

f. For a salicylanilide derivative of formula I wherein $R^1$ is an alkanoyl radical, acylating the corresponding salicylanilide derivative of formula I wherein $R^1$ is a hydrogen atom, by reaction with a reactive derivative of the alkanoic acid.

A particularly suitable reactive derivative of the alkanoic acid is, for example, the anhydride, for example acetic anhydride.

The reaction is preferably carried out in the presence of an organic base, for example, pyridine and conveniently, in the presence of an excess of such base or in an inert organic solvent, at a temperature of from −10° C. to 30° C., preferably at from 0° C. to 25° C.

The salicylanilide derivatives of the invention possess anthelmintic activity and are particularly valuable for the treatment of warm-blooded animals, for example, domestic animals, for example, sheep or cattle, infected with liver fluke, for example, with Fasciola hepatica.

The activity of the salicylanilide derivatives of the invention may be demonstrated by their action in removing Fasciola hepatica from rats, according to a standard test procedure for such activity. In this test the specific salicylanilide derivatives of the invention described in the specification show activity at a minimum dose in the range from 0.1 mg./kg. to 10 mg./kg. when administered orally. In this test no overt toxic effects were detected at the active dose.

Another standard test used to demonstrate activity against liver fluke utilises the action of a test compound in removing Fasciola hepatica from sheep. In this test, for example, 2′,4′-dichloro-5-cyano-3-t-butyl-6-methylsalicylanilide, 2′-trifluoromethyl-4′,5-dicyano-3-t-butyl-6-methylsalicylanide, 2′-bromo-4′-(4-cyanophenylthio)-5-cyano-3-t-butyl-6-methylsalicylanilide, 2′-trifluoromethyl-4′-(4-bromophenylsulphonyl)-5-cyano-3-t-butyl-6-methylsalicylanilide and 2′-trifluoromethyl-4′-(4-chlorophenylsulphonyl)-5-cyano-3-t-butyl-6-methylsalicylanilide show activity at a minimum dose in the range from 0.25 to 2.5 mg./kg. when administered orally or subcutaneously. In this test no overt toxic effects were detected at the active dose.

When used to combat liver fluke infestations in domestic animals, for example, sheep or cattle, the salicylanilide derivatives of the invention are preferably administered orally in the form of a drench such that each animal receives a dose of from 0.25 to 20 mg./kg.

The salicylanilide derivatives of the invention may also be administered by injection or by topical application, in which case a dose of from 0.5 to 20 mg./kg. is appropriate.

The salicylanilide derivatives of the invention are used in the form of conventional anthelmintic compositions, comprising an orally, parenterally or topically acceptable diluent or carrier together with a salicylanilide derivative of the invention, and such a composition is provided as a feature of the invention.

A particularly suitable composition for oral administration is conveniently in the form of a drench, a bolus, tablet, capsule, oily solution or suspension, oil-in-water emulsion, dispersible powder, salt lick, a premix suitable for addition to animal foodstuffs or a mixture with animal foodstuffs. A particularly suitable composition for parenteral administration, is conveniently in the form of a sterile aqueous or oily suspension or solution. A particularly suitable composition for topical administration, is conveniently in the form of a solution containing a solvent, or mixture of solvents, capable of percutaneous absorption which thereby gives rise to systemic distribution of the active agent.

The compositions may be obtained in the conventional manner and using conventional excipients.

The invention is illustrated but not limited by the following Examples.

EXAMPLE 1

Phosphorus trichloride (0.24 g.) is added slowly to a stirred solution of 1.2 g. of 5-cyano-6-methyl-3-t-butylsalicylic acid and 0.84 g. of 2,4-dichloroaniline in 66 g. of chlorobenzene which is maintained at 60° C., and the mixture is then heated under reflux for 4.5 hours. The hot solution is decanted from insoluble matter and evaporated to dryness under reduced pressure. Toluene and petroleum ether (b.p. 60°–80° C.) are successively added and removed by evaporation under reduced pressure, and the residue is cooled (whereupon it solidifies) and stirred with 60 g. of saturated aqueous sodium bicarbonate solution. The mixture is filtered and the solid residue is dried and crystallised from cyclohexane. There is thus obtained 2′,4′-dichloro-5-cyano-6-methyl-3-t-butylsalicylanilide, m.p. 159°–161° C.

The 5-cyano-6-methyl-3-t-butylsalicylic acid used as starting material may be obtained as follows:-

A solution of 16.8 g. of bromine in 105 g. of glacial acetic acid is added during 80 minutes to a stirred solution of 20.8 g. of 6-methyl-3-t-butylsalicylic acid in 190 g. of glacial acetic acid, and the mixture is stirred at laboratory temperature for a further 1 hour and then poured into 500 ml. of an ice-water mixture. The mixture is filtered and there is thus obtained as solid residue 5-bromo-6-methyl-3-t-butylsalicylic acid, m.p. 212°–214° C.

A solution of the above acid in ether is treated with an excess of an ethereal solution of diazomethane, and the mixture is evaporated to dryness. There is thus obtained, quantitatively, methyl 5-bromo-6-methyl-3-t-butylsalicylate, m.p. 54°–58° C.

A mixture of 10.2 g. of the above ester, 4.0 g. of anhydrous cuprous cyanide and 10 ml. of N,N-dimethylformamide is heated under reflux for 75 minutes, cooled and added to a silica gel chromatography column. The column is eluted with a mixture of petroluem ether (b.p. 60°–80° C.) and chloroform, the proportion of chloroform being gradually increased until a 1:1 v/v mixture is used, and the final fractions of eluate are evaporated to dryness. There is thus obtained methyl 5-cyano-6-methyl-3-t-butylsalicylate, m.p. 109°–112° C.

A mixture of 4.8 g. of the above ester, 3.2 g. of potassium hydroxide and 150 ml. of water is stirred and heated at 95° C. for 3 hours and then filtered, and the filtrate is cooled and acidified to pH 2 with dilute aqueous hydrochloric acid. The mixture is filtered and there is thus obtained as solid residue 5-cyano-6-methyl-3-t-butylsalicylic acid, m.p. 215°–217° C. (with decomposition).

EXAMPLE 2

A mixture of 6-methyl-5-p-nitrophenylsulphonyl-3-t-butylsalicylic acid (2.0 g.), 2,4-dibromoaniline (1.3 g.), phosphorus trichloride (0.28 g.) and chlorobenzene (16.5 g.) is stirred and heated under reflux for 90 minutes, and the hot solution is then decanted from insoluble matter and allowed to cool. The mixture is filtered and the solid product is crystallised from acetic acid. There is thus obtained 2',4'-dibromo-6-methyl-5-p-nitrophenylsulphonyl-3-t-butylsalicylanilide, m.p. 205°–206° C.

The process described above is repeated except that 4-nitro-2-trifluoromethylaniline (1.0 g.) is used in place of 2,4-dibromoaniline, and that the mixture is stirred and heated under reflux for 2.5 hours. There is thus obtained 6-methyl-4'-nitro-5-p-nitrophenylsulphonyl-3-t-butyl-2'-trifluoromethylsalicylanilide, m.p. 219°–220° C. after crystallisation from toluene.

The 6-methyl-5-p-nitrophenylsulphonyl-3-t-butylsalicylic acid used as starting material may be obtained as follows:-

Chlorine gas is bubbled into a suspension of 4,4'-dinitrodiphenyl disulphide (6.5 g.) in chloroform (100 g.) which is maintained at 10° C. until a complete solution is obtained, and then for a further 15 minutes. The mixture is evaporated at laboratory temperature and under reduced pressure until the excess of chlorine gas and one-sixth of the chloroform has been removed. The resulting solution of p-nitrobenzenesulphenyl chloride is added during 15 minutes to a mixture of 6-methyl-3-t-butylsalicylic acid (8.4 g.), pyridine (6.85 g.) and tetrachloroether (156 g.) from which moisture is rigorously excluded, and the mixture is stirred at laboratory temperature for 16 hours. The mixture is washed with water and then extracted three times with 100 g. of 4% aqueous sodium hydroxide solution each time. The combined extracts are acidifed with aqueous hydrochloric acid and extracted with ether, and the ethereal extract is dried and evaporated to dryness. The residue is crystallised from xylene and there is thus obtained 6-methyl-5-p-nitrophenylthio-3-t-butylsalicylic acid, m.p. 182°–185° C.

A mixture of the above acid (3.0 g.), acetic acid (30 g.) and 30% w/v aqueous hydrogen peroxide solution (18.5 g.) is heated at 90°–95° C. for 40 minutes and then poured into water (100 ml.). The mixture is filtered and the solid product is crystallised from toluene. There is thus obtained 6-methyl-5-p-nitrophenylsulphonyl-3-t-butysalicylic acid, m.p. 222°–224° C.

EXAMPLE 3

The process described in Example 1 is repeated except that an aniline derivative of the formula:-

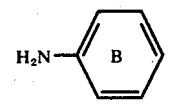

is used in place of 2,4-dichloroaniline. There are thus obtained the compounds described in the following table:-

| Compound No. | Ring B substituent(s) | m.p. (° C.) |
|---|---|---|
| 1 | 3,5-dichloro | 247–249 (d) |
| 2 | 3,5-bistrifluoromethyl | 266–270 (d) |
| 3 | 4-cyano-2-trifluoromethyl | 169–171 |
| 4 | 2-chloro-4-cyano | 189–191 |
| 5 | 4-bromo-2-trifluoromethyl | 200–202 |
| 6 | 4-p-chlorobenzoyl | 197.5–199.5 |

EXAMPLE 4

A mixture of 5-bromo-4'-iodo-6-methyl-3-t-butylsalicylanilide (3.2 g.; m.p. 138°–141° C.; prepared from 5-bromo-6-methyl-3-t-butylsalicylic acid and 4-iodoaniline by a similar process to that described in Example 1), cuprous cyanide (1.5 g.) and dimethylformamide (10 ml.) is heated under reflux for 90 minutes, cooled and evaporated to small volume under reduced pressure. The residue is absorbed onto kieselguhr and the mixture is added to a silica gel column and chromatographed using chloroform as eluant. The appropriate fractions of the eluate are combined and concentrated to small bulk (which contains three components), and this solution is again chromatographed using a similar chromatography system but with a 1:99 v/v mixture of ethyl acetate and chloroform as eluant. The appropriate fractions of the eluate are combined and evaporated to dryness and the residue is triturated with ether. There is thus obtained 4',5-dicyano-6-methyl-3-t-butylsalicylanilide, m.p. 184°–192° C.

EXAMPLE 5

Trifluoroacetic acid (8 ml.) is added to a mixture of 2',6-dimethyl-4'-nitro-3-t-butylsalicylanilide (1.71 g.) and hexamethylene tetramine (0.70 g.), and after the initial exothermic reaction has subsided the mixture is heated under reflux for 16 hours, cooled and poured into a mixture of ice and water (75 ml.). The mixture is basified to pH 6–7 with saturated aqueous sodium bicarbonate solution and then filtered. The solid residue is purified by chromatography on a silica gel column using a 9:1 v/v mixture of chloroform and ethyl acetate as eluant. The appropriate fractions of the eluate are combined and evaporated to dryness and the residue is crystallised from ether. There is thus obtained 5-formyl-2′,6-dimethyl-4′-nitro-3-t-butylsalicylanilide, m.p. 185°–187° C.

EXAMPLE 6

The process described in Example 1 is repeated except that 5-acetyl-6-methyl-3-t-butylsalicylic acid and either 2-chloro-4-nitroaniline or 4-nitro-2-trifluoromethylaniline are used as starting materials. The hot reaction mixture after decantation is cooled and diluted with petroleum ether (b.p. 40°–60° C.) until turbid. The mixture is further cooled and filtered, and the solid product is crystallised from a mixture of toluene and petroleum ether (b.p. 80°–100° C.) There are thus respectively obtained 5-acetyl-2′-chloro-6-methyl-4′-nitro-3-t-butylsalicylanilide, m.p. 182°–183° C., and 5-acetyl-6-methyl-4′-nitro-3-t-butyl-2′-trifluoromethylsalicylanilide, m.p. 178°–179° C.

The 5-acetyl-6-methyl-3-t-butylsalicylic acid used as starting material may be obtained as follows:-

A solution of acetyl chloride (40 ml.) in ethylene dichloride (50 ml.) is added to a stirred suspension of aluminum chloride (40 g.) in ethylene dichloride (200 ml.) which is cooled to −20° C., and the mixture is stirred at that temperature for 20 minutes. A suspension of 6-methyl-3-t-butylsalicylic acid (50 g.) in ethylene dichloride (220 ml.) is added during 30 minutes, the temperature being kept at −20° C. during the addition, and the stirred mixture is allowed to warm to −3° C. during 90 minutes and is stirred at that temperature for 45 minutes and then poured into a mixture of ice and dilute aqueous hydrochloric acid. The mixture is extracted with a 1:1 v/v mixture of ethyl acetate and ether and the extract is dried and evaporated to dryness. The residue is dissolved in dilute aqueous sodium hydroxide solution and the solution is heated at 90° C. for 5 minutes, filtered, cooled and acidifed with dilute aqueous hydrochloric acid. The mixture is extracted with ether and the extract is dried and evaporated to dryness. The residue is repeatedly dissolved in toluene and the toluene is removed by evaporation until all acetic acid has been removed. The residue is crystallised from cyclohexane and there is thus obtained 5-acetyl-6-methyl-3-t-butylsalicylic acid, m.p. 137°–138° C.

EXAMPLE 7

A cooled aqueous solution of benzenediazonium chloride (prepared from 0.31 g. of aniline, 0.24 g. of sodium nitrate and 3.3 ml. of hydrochloric acid by conventional means) is added dropwise to a stirred mixture of 6-methyl-4′-nitro-3-t-butyl-2′-trifluoromethylsalicylanilide (1.2 g.; m.p. 143°–145° C.; prepared from 6-methyl-3-t-butylsalicylic acid and 4-nitro-2-trifluoromethylanine by a similar process to that described in Example 1), aqueous 2.5N-sodium hydroxide solution (30Ml.) and ethanol (15 ml.) which is cooled to between 0° and 5° C. The mixture is stirred for 10 minutes and then poured into a mixture of ice and 50 ml. of aqueous 2N-hydrochloric acid. The mixture is filtered and the solid product crystallised from cyclohexane. There is thus obtained 6-methyl-4′-nitro-5-phenylazo-3-t-butyl-2′-trifluoromethylsalicylanilide, m.p. 151°–153° C.

The process described above is repeated except that a 5-unsubstituted salicylanilide derivative of the formula:-

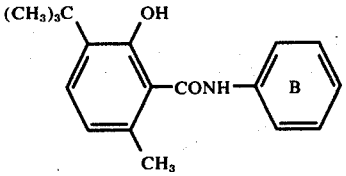

and a benzenediazonium chloride of the formula:-

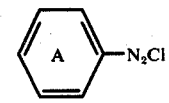

are used as starting materials. There are thus obtained the compounds described in the following table:-

| Compound No. | Ring A substituent(s) | Ring B substituent(s) | m.p. (° C.) |
|---|---|---|---|
| 1 | — | 2-methyl-4-nitro | 216–217 |
| 2 | — | 2-chloro-4-nitro | 187–189 |
| 3 | 4-chloro | 4-nitro | 112–113 |
| 4 | 4-chloro | 2-methyl-4-nitro | 221–223 |
| 5 | 4-nitro | 3,5-bistrifluoromethyl | 262–264 |
| 6 | 4-chloro-2-methyl | 2-chloro-4-nitro | 201–203 |
| 7 | 3,5-dichloro | 2-chloro-4-nitro | 228–230 |
| 8 | 4-chloro | 2-chloro-4-nitro | 198–200 |
| 9 | 4-chloro-2-trifluoromethyl | 2-chloro-4-nitro | 156–158 |
| 10 | 4-bromo | 2-chloro-4-nitro | 212–214 |
| 11 | 4-chloro | 4-nitro-2-trifluoromethyl | 190–191 |
| 12 | 4-bromo | 4-nitro-2-trifluoromethyl | 209–211 |
| 13 | 4-bromo | 4-cyano | 219–222 |

The 5-unsubstituted salicylanilide derivatives used as starting material may be obtained from an aniline of the formula:-

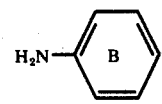

and 6-methyl-3-t-butylsalicylic acid by a similar process to that described in Example 1, and are characterised as follows:-

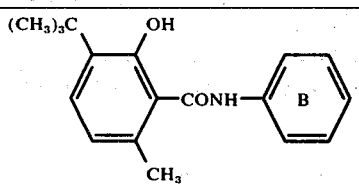

| Compound No. | Ring B substituent(s) | m.p. (° C.) |
|---|---|---|
| 1 | 2-methyl-4-nitro | 126–127 |
| 2 | 2-chloro-4-nitro | 135–137 |
| 3 | 4-nitro | 176–178 |
| 4 | 3,5-bistrifluoromethyl | 159–160 |
| 5 | 4-cyano | 175–176 |

EXAMPLE 8

Using essentially the same procedure as that described in the first part of Example 2, but using a 5-arylthiosalicylic acid of the formula:-

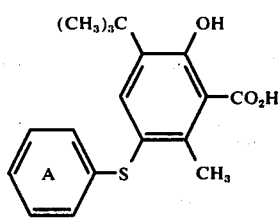

and an aniline of the formula:-

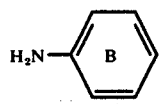

there are obtained the salicylanilides of the formula:-

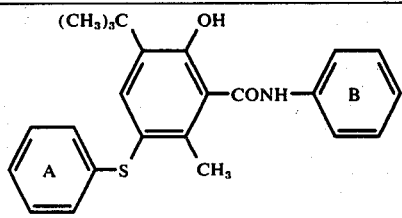

| Compound No. | Ring A substituent(s) | Ring B substituent(s) | m.p. (° C.) |
|---|---|---|---|
| 1 | 3,4-dichloro | 2-trifluoromethyl-4-nitro | 104 |
| 2 | 3,4-dichloro | 2-chloro-4-nitro | 145–146 |
| 3 | 4-cyano | 2-chloro-4-nitro | 143–144 |
| 4 | 2,4,5-trichloro | 2-chloro-4-nitro | 186–188 |
| 5 | — | 2-trifluoromethyl-4-nitro | 151–152 |
| 6 | 2-nitro-4-chloro | 2-chloro-4-nitro | 192–193 |
| 7 | 2-chloro-5-nitro | 2-chloro-4-nitro | 184–185 |
| 8 | 2,5-dichloro | 2-chloro-4-nitro | 159–161 |
| 9 | 2,5-dichloro | 2-trifluoromethyl-4-nitro | 168–170 |
| 10 | 3-methyl-4-bromo | 2-chloro-4-nitro | 125–127 |
| 11 | 3-methyl-4-bromo | 2-trifluoromethyl-4-nitro | 127–128 |
| 12 | 3-chloro-4-methoxy | 2-trifluoromethyl-4-nitro | 146–148 |
| 13 | 4-chloro | 2-chloro-4-nitro | 124–125 |
| 14 | 4-chloro | 2-trifluoromethyl-4-nitro | 148–149 |
| 15 | 4-bromo | 2-chloro-4-nitro | 160–162 |
| 16 | 4-bromo | 2-trifluoromethyl-4-nitro | 139–141 |
| 17 | 2-nitro | 2-trifluoromethyl-4-nitro | 166–168 |
| 18 | 3-nitro | 2-chloro-4-nitro | 120–121 |
| 19 | 2,4-dinitro | 2,4-dibromo | 168–169 |
| 20 | 2,4-dinitro | 2-chloro-4-nitro | 184–185 |
| 21 | 2,4-dinitro | 2-trifluoromethyl-4-nitro | 199–200 |
| 22 | 4-nitro | 2-chloro-4-nitro | 189–190 |
| 23 | 4-nitro | 2-bromo-4-nitro | 180–182 |
| 24 | 4-nitro | 2-trifluoromethyl-4-nitro | 183–185 |
| 25 | 4-nitro | 2-chloro-4-cyano | 227–228 |
| 26 | 4-nitro | 2-trifluoromethyl-4-cyano | 194–195 |

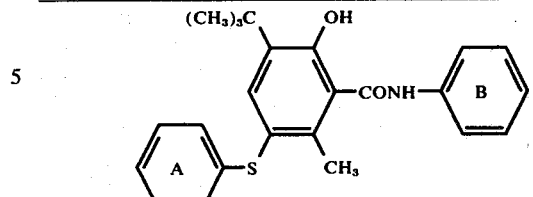

The following 5-arylthiosalicylic acids of the formula set out above and used as starting materials, are obtained in a similar manner to that described in Example 2 for 5-(4-nitrophenylthio)-3-t-butyl-6-methylsalicylic acid, but using a diphenyl disulphide of the formula:-

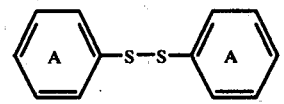

and 3-t-butyl-6-methylsalicylic acid:-

| Acid No. | Ring A substituent(s) | m.p. (° C.) |
|---|---|---|
| 1* | 3,4-dichloro | 163–164 |
| 2* | 4-cyano | 207–208 |
| 3* | 2,4,5-trichloro | 216–218 |
| 4* | — | 169–170 |
| 5 | 2-nitro-4-chloro | 223–225 |
| 6 | 2-chloro-5-nitro | 220–221 |
| 7* | 2,5-dichloro | 202–204 |
| 8* | 3-methyl-4-bromo | 193–195 |
| 9* | 3-chloro-4-methoxy** | 167–169 |
| 10* | 4-chloro | 172–174 |
| 11* | 4-bromo | 172–174 |
| 12 | 2-nitro | 218–220 |
| 13 | 3-nitro | 185–188 |
| 14 | 2,4-dinitro | 258 (dec.) |

*In these cases, 2,6-lutidine is used instead of pyridine for the reaction of the arylsulphenyl chloride with 6-methyl-3-t-butylsalicylic acid.
**The original starting material in this case is 4,4''-dimethoxydiphenyl disulphide and ring chlorination occurs during the preparation of the arylsulphenyl chloride.

EXAMPLE 9

Phosphorus trichloride (0.225 ml.) is added to a stirred suspension of 5-cyano-3-t-butyl-6-methylsalicylic acid (1.5 g.) and 4-amino-4'-bromo-3-trifluoromethyldiphenyl sulphide (2.24 g.) in chlorobenzene (100 ml.) at 60° C. The mixture is heated under reflux for approximately 7 hours, during which time the course of the reaction is followed by analysis of the reaction mixture by thin layer chromatography (TLC) on silica gel using chloroform as eluant. The hot supernatant liquor is decanted from a gummy residue and is evaporated to dryness under reduced pressure to give an oily solid. This solid is first washed with boiling petroleum ether (b.p. 60°–80° C.) (3 × 30 ml.) and is then crystallised from aqueous methanol to give 2'-trifluoro-4'-(4-bromophenylthio)-5-cyano-3-t-butyl-6-methylsalicylanilide, m.p. 211°–215° C. Further purification by recrystallisation from a mixture of methanol and ethyl acetate gives material having m.p. 213°–215° C.

In a similar manner, starting with an aniline of the formula:-

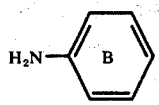

there are obtained the following salicylanilides of the formula:-

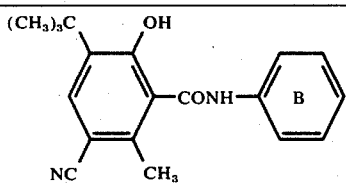

| Compound No. | Ring B substituent(s) | m.p. (° C.) |
|---|---|---|
| 1 | 2-iodo-4-chloro | 157–158 |
| 2 | 3,4-dichloro | 185–186 |
| 3 | 4-bromo | 122–125 |
| 4 | 2,4-dibromo | 176–178 |
| 5 | 2-iodo-4-bromo | 149–150 |
| 6 | 2,4,5-trichloro | 195–197 |
| 7 | 3,4,5-trichloro | 253–254 |
| 8 | 3-cyano-4-chloro | 220–222 |
| 9 | 2-chloro-5-cyano | 167–169 |
| 10 | 2-iodo-4-cyano | 192–194 |
| 11 | 2-bromo-4-cyano | 187–189 |
| 12 | 2-i-propyl-4-cyano | 231–235 |
| 13 | 3-chloro-4-cyano | 130–140 |
| 14 | 3,5-dichloro-4-cyano | 288–290 |
| 15 | 2-methyl-4-nitro | 203–205 |
| 16 | 2-cyano-4-nitro | 115–120 |
| 17 | 2-trifluoromethyl-4-(4-cyanophenoxy) | 219–221 |
| 18 | 3-chloro-4-(4-bromophenoxy) | 109–110 |
| 19 | 3,5-dichloro-4(4-fluorophenoxy) | 233–235 |
| 20 | 3,5-dichloro-4-(4-chlorophenoxy) | 231–233 |
| 21 | 3,5-dichloro-4-(4-bromophenoxy) | 233–236 |
| 22 | 3,5-dichloro-4-(2,4-dichlorophenoxy) | 216–219 |
| 23 | 3,5-dichloro-4-(2,5-dichlorophenoxy) | 160 (decomposition) |
| 24 | 2-bromo-3,5-dichloro-4-(3,4-dichlorophenoxy) | 104–106 |
| 25 | 3,5-dichloro-4-(2-chlorophenoxy) | 157–159 |
| 26 | 4-(4-chlorophenylthio) | 159–161 (decomposition) |
| 27 | 4-(4-bromophenylthio) | 122–124 |
| 28 | 4-(4-cyanophenylthio) | 196–198 |
| 29 | 4-(4-nitrophenylthio) | 140–142 |
| 30 | 2-bromo-4-(4-cyanophenylthio) | 147–150 (decomposition) |
| 31 | 2-bromo-4-(4-nitrophenylthio) | 111–114 |
| 32 | 2-trifluoromethyl-4-(4-cyanophenylthio) | 166–169 |
| 33 | 3,5-dichloro-4-(4-chlorophenylthio) | 227–229 |
| 34 | 3,5-dichloro-4-(4-bromophenylthio) | 240–242 |

EXAMPLE 10

Using a similar procedure to that described in the first part of Example 2, there is obtained from 5-(4-nitrophenylsulphinyl)-3-t-butyl-6-methylsalicylic acid, the compound 2'-chloro-4'-nitro-5-(4-nitrophenylsulphinyl)-3-t-butyl-6-methylsalicylanilide, m.p. 225°–226° C.

The starting 5-(4-nitrophenylsulphinyl)-3-t-butyl-6-methylsalicylic acid is obtained as follows:-

A solution of 5-(4-nitrophenylthio)-3-t-butyl-6-methylsalicylic acid (2.0 g.) in acetic acid (200 ml.) is mixed with 30% w/v aqueous hydrogen peroxide solution (11 ml.). The mixture is stirred at room temperature for 6 hours and then added to water (700 ml.). The precipitated solid thus formed is separated by filtration and crystallised from acetic acid to give 5-(4-nitrophenylsulphinyl)-3-t-butyl-6-methylsalicylic acid, m.p. 201°–202° C.

EXAMPLE 11

30% w/v Aqueous hydrogen peroxide solution (1.5 ml.) is added to a solution of 2'-chloro-4'-nitro-5-(2,4,5-trichlorophenylthio)-3-t-butyl-6-methylsalicylanilide (0.4 g.) in acetic acid (15 ml.) at 50°–60° C. The mixture is heated at 95°–100° C. for 30 minutes and is then poured into ice cold water (200 ml.). The precipitated solid thus obtained is crystallised twice from acetic acid to give 2'-chloro-4'-nitro-5-(2,4,5-trichlorophenylsulphinyl)-3-t-butyl-6-methylsalicylanilide, m.p. 245°–246° C.

In a similar manner, but starting from 2'-trifluoromethyl-4'-nitro-5-(2,4,5-trichlorophenylthio)-3-t-butyl-6-methylsalicylanilide, there is obtained 2'-trifluoromethyl-4'-nitro-5-(2,4,5-trichlorophenylsulphinyl)-3-t-butyl-6-methylsalicylanilide, m.p. 234°–235° C.

The starting material 2'-trifluoromethyl-4'-nitro-5-(2,4,5-trichlorophenylthio)-3-t-butyl-6-methylsalicylanilide, m.p. 179°–180° C., is obtained using a similar procedure to that described in the first part of Example 2, but starting from 5-(2,4,5-trichlorophenylthio)-3-t-butyl-6-methylsalicylic acid and 2-trifluoromethyl-4-nitro-aniline.

EXAMPLE 12

30% w/v Aqueous hydrogen peroxide solution (70 μl.) is added to a suspension of 2'-trifluoromethyl-4'-(4-bromophenylthio)-5-cyano-3-t-butyl-6-methylsalicylanilide (0.25 g.) in acetic acid (4 ml.), and the mixture heated at 70°–80° C. for 1 hour. Water (2 ml.) is then added and the solution is cooled slowly to room temperature. The crystalline solid which is thus obtained is separated by filtration and dried to give 2'-trifluoromethyl-4'-(4-bromophenylsulphinyl)-5-cyano-3-t-butyl-6-methylsalicylanilide, m.p. 178°–180° C.

In a similar manner, there are obtained 2'-trifluoromethyl-4'-(4-chlorophenylsulphinyl)-5-cyano-3-t-butyl-6-methylsalicylanilide, m.p. 192°–199° C., 4'-(4-bromophenylsulphinyl)-5-cyano-3-t-butyl-6-methylsalicylanilide, m.p. 140°–145° (decomposes; softens from 130° C.), 4'-(4-chlorophenylsulphinyl)-5-cyano-3-t-butyl-6-methylsalicylanilide, m.p. 217°–219° C., from the starting materials 2'-trifluoromethyl-4'-(4-chlorophenylthio)-, 4'-(4-bromophenylthio)-, and 4'-(4-chlorophenylthio)-5-cyano-3-t-butyl-6-methylsalicylanilide respectively.

The starting material, 2'-trifluoromethyl-4'-(4-chlorophenylthio)-5-cyano-3-t-butyl-6-methylsalicylanilide, m.p. 193°–195° C., is obtained using a similar procedure to that described in Example 9.

EXAMPLE 13

Using a similar procedure to that described in the first part of Example 2, but using a 5-arylsulphonylsalicylic acid of the formula:-

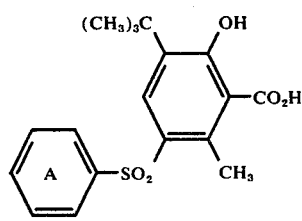

and an aniline of the formula:-

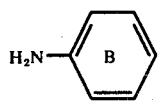

there are obtained the following compounds of the formula:-

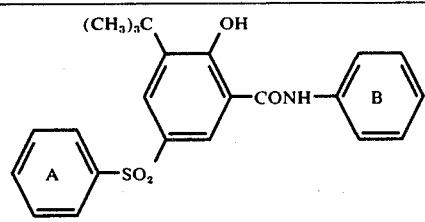

| Compound No. | Ring A substituent(s) | Ring B substituent(s) | m.p. (° C.) |
|---|---|---|---|
| 1 | 4-nitro | 2-chloro-4-nitro | 217–219 |
| 2 | 4-nitro | 2-chloro-4-cyano | 214–215 |
| 3 | 4-nitro | 2-trifluoromethyl-4-bromo | 189–190 |
| 4 | 4-nitro | 2-bromo-4-nitro | 193–194 |
| 5 | 4-nitro | 2-trifluoromethyl-4-cyano | 116–117 |
| 6 | 4-nitro | 4-nitro | 197–198 |
| 7 | 4-nitro | 2-methyl-4-nitro | 207–208 |
| 8 | 2-nitro-4-chloro | 2-chloro-4-nitro | 220–221 |
| 9 | 2-nitro-4-chloro | 2-trifluoromethyl-4-nitro | 163–164 |
| 10 | 3-nitro | 2-chloro-4-nitro | 189–190 |
| 11 | 2,4-dinitro | 2-trifluoromethyl-4-nitro | 216–217 |
| 12 | 4-chloro | 2-chloro-4-nitro | 231–232 |
| 13 | 4-chloro | 2-trifluoromethyl-4-nitro | 189–190 |
| 14 | 4-bromo | 2-chloro-4-nitro | 225–226 |
| 15 | 4-bromo | 2-trifluoromethyl-4-nitro | 189–191 |
| 16 | 4-methyl | 2-chloro-4-nitro | 194–196 |
| 17 | 4-methyl | 2-trifluoromethyl-4-nitro | 127–128 |
| 18 | 3-methyl-4-bromo | 2-chloro-4-nitro | 200–201 |
| 19 | 3-methyl-4-bromo | 2-trifluoromethyl-4-nitro | 184–186 |
| 20 | 3-chloro-4-methoxy | 2-chloro-4-nitro | 201–202 |
| 21 | 3-chloro-4-methoxy | 2-trifluoromethyl-4-nitro | 122–123 |
| 22 | — | 2-chloro-4-nitro | 202–204 |
| 23 | — | 2-trifluoromethyl-4-nitro | 207–208 |
| 24 | 3,4-dichloro | 2-chloro-4-nitro | 197–199 |
| 25 | 3,4-dichloro | 2-trifluoromethyl-4-nitro | 179–180 |

The 5-arylsulphonylsalicylic acids used as starting materials are prepared by oxidation of a 5-arylthiosalicylic acid of the formula:-

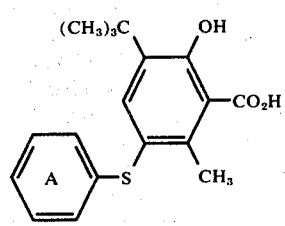

using a similar procedure to that described in Example 2 for the preparation of 5-(4-nitrophenylsulphonyl)-3-t-butyl-6-methylsalicylic acid, to give compounds of the formula:-

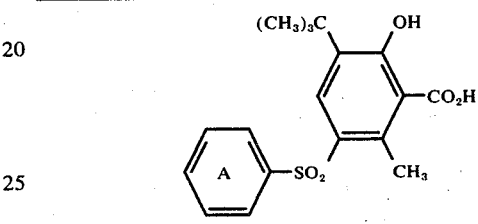

| Acid No. | Ring A substituent | m.p. (° C.) |
|---|---|---|
| 1 | 2-nitro-4-chloro | 244–245 |
| 2 | 3-nitro | 190–191 |
| 3 | 2,4-dinitro | 240 (decomposition) |
| 4 | 4-chloro | 196–197 |
| 5 | 4-bromo | 198–200 |
| 6 | 4-methyl | 187–188 |
| 7 | 3-methyl-4-bromo | 192–194 |
| 8 | 3-chloro-4-methoxy | 191–193 |
| 9 | — | 172–174 |
| 10 | 3,4-dichloro | 191–192 |

The starting material 5-(4-methylphenylthio)-3-t-butyl-6-methylsalicylic acid, m.p. 163°–164° C. is obtained in a similar manner to that described in Example 2 for 5-(4-nitrophenylthio)-3-t-butyl-6-methylsalicylic acid but starting from di-p-tolyldisulphide and 3-t-butyl-6-methylsalicylic acid.

EXAMPLE 14

30% w/v Aqueous hydrogen peroxide solution (0.16 ml.) is added to a suspension of 2'-trifluoromethyl-4'-(4-bromophenylthio)-5-cyano-3-t-butyl-6-methylsalicylanilide (0.25 g.) in acetic acid (3 ml.). The mixture is heated at 95°–100° C. for 1.5 hours to give a clear solution. This solution is cooled slowly to room temperature and the solid thus obtained is collected and dried to give 2'-trifluoromethyl-4'-(4-bromophenylsulphonyl)-5-cyano-3-t-butyl-6-methylsalicylanilide, m.p. 221°–223° C.

In a similar manner, but starting with the corresponding arylthio substituted salicylanilide, there are obtained the compounds of the following formula:-

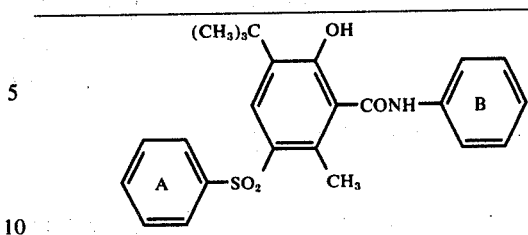

| Compound No. | Ring B substituent(s) | m.p. (° C.) |
|---|---|---|
| 1 | 4-(4-chlorophenylsulphonyl) | 230–232 |
| 2 | 4-(4-bromophenylsulphonyl) | 232–234 (decomposition) |
| 3 | 2-trifluoromethyl-4-phenylsulphonyl | 219–221 |
| 4 | 3,5-dichloro-4-phenylsulphonyl | 273–275 |
| 5 | 2-trifluoromethyl-4-(4-chlorophenyl-sulphonyl) | 216–219 |

The starting materials, 2'-trifluoromethyl-4'-phenylthio-5-cyano-3-t-butyl-6-methylsalicylanilide, m.p. 147°–150° C., and 3',5'-dichloro-4'-phenylthio-5-cyano-3-t-butyl-6-methylsalicylanilide, m.p. 227°–229° C., are obtained using a similar procedure to that described in Example 9, but starting with 2-trifluoromethyl-4-phenylthio- and 3,5-dichloro-4-phenylthio-aniline respectively.

EXAMPLE 15

30% w/v Aqueous hydrogen peroxide solution (3.8 ml.) is added to a suspension of 2'-chloro-4'-nitro-5-phenylthio-3-t-butyl-6-methylsalicylanilide (0.85 g.) in acetic acid (10 ml.). The mixture is heated at 95°–100° C. for 1 hour to give a yellow solution. The hot solution is poured into cold water (100 ml.) and the mixture is stirred overnight. The white solid which has formed is separated by filtration and is recrystallised from acetic acid to give 2'-chloro-4'-nitro-5-phenylsulphonyl-3-t-butyl-6-methylsalicylanilide, m.p. 202°–204° C.

In a similar manner, but starting from the corresponding 5-arylthiosalicylanilide of the formula:-

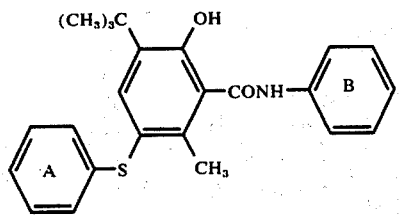

there are obtained the compounds of the formula:-

| Compound No. | Ring A substituent(s) | Ring B substituent(s) | m.p. (° C.) |
|---|---|---|---|
| 1 | 4-nitro | 2-chloro-4-nitro | 217–219 |
| 2 | 4-nitro | 2-chloro-4-cyano | 214–215 |
| 3 | 4-nitro | 2-bromo-4-nitro | 193–194 |
| 4 | 4-nitro | 2-trifluoromethyl-4-cyano | 116–117 |
| 5 | 2-nitro-4-chloro | 2-chloro-4-nitro | 220–221 |
| 6 | 3-nitro | 2-chloro-4-nitro | 188–190 |
| 7 | 4-chloro | 2-chloro-4-nitro | 231–232 |
| 8 | 4-chloro | 2-trifluoromethyl-4-nitro | 189–190 |
| 9 | 4-bromo | 2-chloro-4-nitro | 225–226 |
| 10 | 4-bromo | 2-trifluoromethyl-4-nitro | 189–191 |
| 11 | 3-methyl-4-bromo | 2-chloro-4-nitro | 200–201 |
| 12 | 3-methyl-4-bromo | 2-trifluoromethyl-4-nitro | 184–186 |
| 13 | 3-chloro-4-methoxy | 2-trifluoromethyl-4-nitro | 122–123 |
| 14 | — | 2-trifluoromethyl-4-nitro | 207–208 |
| 15 | 3,4-dichloro | 2-chloro-4-nitro | 197–199 |
| 16 | 3,4-dichloro | 2-trifluoromethyl-4-nitro | 179–180 |

The starting material, 2'-chloro-4'-nitro-5-phenylthio-3-t-butyl-6-methylsalicylanilide, is obtained as a crystalline solid, m.p. 119°–120° C., from the reaction of 5-phenylthio-3-t-butyl-6-methylsalicylic acid and 2-chloro-4-nitro-aniline using a similar procedure to that described in the first part of Example 2.

EXAMPLE 16

Using a similar procedure to that described in the first part of Example 7, and starting from a 5-unsubstituted salicylanilide of the formula:-

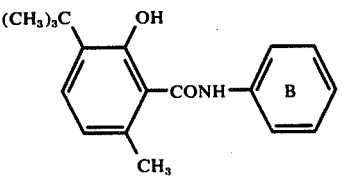

there are obtained the following 5-arylazo-salicylanilides of the formula:-

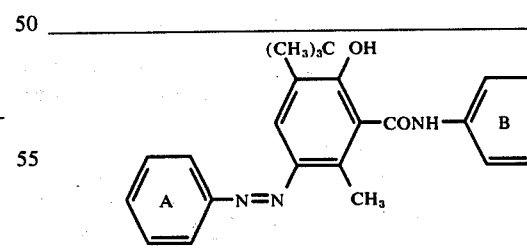

| Compound No. | Ring A substituent | Ring B substituent | m.p. (° C.) |
|---|---|---|---|
| 1 | 4-nitro | 2,4-dichloro | 186–188 |
| 2 | 4-nitro | 4-nitro | 226–230 |
| 3 | 4-cyano | 2-methyl-4-nitro | 254–257 |
| 4 | 4-cyano | 4-(4-nitrophenylthio) | 143–146 |
| 5 | 2-chloro-6-methyl | 4-cyano | 179–182 |
| 6 | 2,6-dimethyl | 4-cyano | 178–179 |

The 5-unsubstituted salicylanilide derivatives used as starting materials are obtained from the corresponding aniline of the formula:-

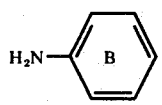

and 3-t-butyl-6-methylsalicylic acid, using a similar procedure to that described in the first part of Example 9, and have the following properties:-

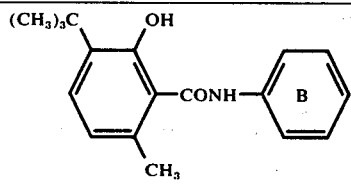

| Material No. | Ring B substituent(s) | m.p. (° C.) |
|---|---|---|
| 1 | 2,4-dichloro | 123–125 |
| 2 | 4-(4-nitrophenylthio) | 149–151 |

EXAMPLE 18

Using a similar procedure to that described in the first part of Example 2, but using a 5-arylthiosalicylic acid of the formula:-

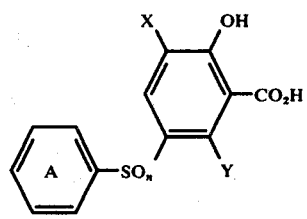

together with the corresponding aniline of the formula:-

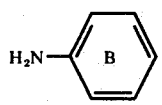

there are obtained the salicylanilides of the formula:-

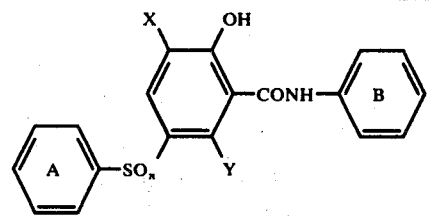

| Compound No. | n | Ring A substituent(s) | X | Y | Ring B substituent(s) | m.p. (° C.) |
|---|---|---|---|---|---|---|
| 1 | 0 | 4-nitro | i-propyl | methyl | 2-chloro-4-nitro | 152–155 |
| 2 | 2 | 4-nitro | i-propyl | methyl | 2-chloro-4-nitro | 214–216 |
| 3 | 2 | 4-chloro | i-propyl | methyl | 2-chloro-4-nitro | 195–197 |
| 4 | 0 | 4-nitro | t-butyl | hydrogen | 2-chloro-4-nitro | 214–216 |
| 5 | 0 | 4-nitro | t-butyl | hydrogen | 2-trifluoromethyl-4-nitro | 210–212 |
| 6 | 2 | 4-nitro | t-butyl | hydrogen | 2-chloro-4-nitro | 210–212 |

EXAMPLE 17

A solution of acetic anhydride (0.1 ml.) in dry pyridine (1 ml.) is added dropwise to a stirred solution of 2'-trifluoromethyl-4',5-dicyano-3-t-butyl-6-methylsalicylanilide (0.38 g.) in dry pyridine (4 ml.) at 0°–5° C. The mixture is stirred at 0°–5° C. for 1 hour and then at room temperature until no starting salicylanilide is left, as shown by the absence of the characteristic ferric chloride positive shot, on TLC analysis on silica using chloroform as eluant. The mixture is then poured onto a mixture of ice (30 g.) and 2N hydrochloric acid solution (20 ml.). The solid which is formed is collected and washed with water. After drying, the solid is recrystallised from a mixture containing equal parts of ether and cyclohexane to give 2-O-acetyl-2'-trifluoromethyl-4',5-dicyano-3-t-butyl-6-methylsalicylanilide, m.p. 171°–172° C., having spectroscopic properties consistent with those of an O-acetate.

Those of the starting materials which are 5-arylthiosalicylic acids may be prepared using a similar procedure to that described for 5-(4-nitrophenylthio)-3-t-butyl-6-methylsalicylic acid in Example 2, except that pyridine is replaced by 2,6-lutidine in the preparation of the arylsulphenyl chloride. Thus there are obtained 5-(4-nitrophenylthio)-3-isopropyl-6-methylsalicylic acid, m.p. 177°–179° C. and 5-(4-nitrophenylthio)-3-t-butylsalicylic acid, m.p. 184°–185° C., from the reaction of 4-nitrophenylsulphenyl chloride with 3-isopropyl-6-methylsalicylic acid and 3-t-butylsalicylic acid respectively.

The starting materials, 5-(4-nitrophenylsulphonyl)-3-isopropyl-6-methylsalicylic acid, m.p. 214°–216° C. and 5-(4-nitrophenylsulphonyl)-3-t-butylsalicylic acid, m.p. 199°–201° C., are obtained by oxidation of the above 5-arylthiosalicylic acids using a similar procedure to that described in Example 2 for the preparation of 5-(4-nitrophenylsulphonyl)-3-t-butyl-6-methylsalicylic acid.

The remaining starting material, 5-(4-chlorophenylsulphonyl)-3-isopropyl-6-methylsalicylic acid, is obtained as follows:-

4-Chlorophenylsulphonyl chloride (6.3 g.) is added to a mixture of aluminum chloride (8.1 g.) and 3-isopropyl-6-methylsalicylic acid (5.7 g.) in dry nitrobenzene (3 ml.). The mixture is heated at 95°–100° C. for 4 hours and is then stirred into a mixture of ice (250 g.) and concentrated hydrochloric acid (30 ml.). The mixture is subsequently extracted with ethyl acetate (3 × 250 ml.). The extracts are washed with water and are then concentrated in vacuo. Residual nitrobenzene is removed by steam distillation. The oily solid, which remains after decantation of the water from the distillation residue, is crystallised from a mixture of xylene and petroleum ether (b.p. 60°–80° C.) to give 5-(4-chlorophenylsulphonyl)-3-isopropyl-6-methylsalicylic acid, m.p. 165°–166° C.

EXAMPLE 19

Compositions suitable for use as experimental aqueous drenches may be prepared using the following procedure:-

A mixture containing the required amount of a salicylanilide derivative (up to 8% w/v) as described in any of the Examples 1–18, aluminium magnesium silicate flake (high viscosity form; 0.8% w/v), sodium carboxymethylcellulose (0.9% w/v), methyl-p-hydroxybenzoate (0.15% w/v), n-propyl p-hydroxybenzoate (0.015% w/v), sodium citrate (0.5% w/v), and a condensate (0.1% w/v) of the oleate ester of sorbitol and of its anhydrides with approximately 20 molecular proportions of ethylene oxide, in water (to 100%) is ball-milled for 30 minutes. The resultant suspension is then used as an aqueous drench.

What we claim is:
1. A salicylanilide derivative having the formula:-

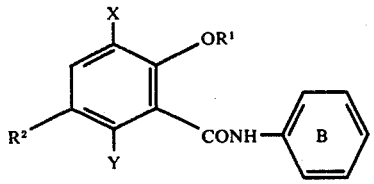

wherein $R^1$ is hydrogen; $R^2$ is a cyano radical; X is a tertiary butyl radical; Y is a methyl radical; and ring B forms a phenyl radical bearing a halogen atom or a trifluoromethyl radical at the 2-position and a nitro or cyano radical at the 4-position; or ring B forms a phenyl radical bearing in either the 3- or 4-positions or the 3,4- and 5-positions, substituents selected from halogen atoms, cyano, nitro and trifluoromethyl radicals, alkyl radicals of from 1 to 4 carbon atoms, and phenoxy, phenylthio phenylsulphonyl, and benzoyl radicals each optionally bearing one or two substituents selected from halogen atoms and cyano and nitro radicals, provided that at least one of the substituents borne by ring B is a cyano radical or a halogen atom; or a base-addition salt thereof.

2. A salicylanilide derivative according to claim 1 which is 3'-chloro-4',5-dicyano-3-t-butyl-6-methylsalicylanilide or a base-addition salt thereof.

3. A salicylanilide derivative according to claim 1 which is 2'-trifluoromethyl-4',5-dicyano-3-t-butyl-6-methylsalicylanilide, or a base-addition salt thereof.

4. A salicylanilide derivative according to claim 1 which is 2'-bromo-4',5-dicyano-3-t-butyl-6-methylsalicylanilide, or a base-addition salt thereof.

5. A salicylanilide derivative having the formula:

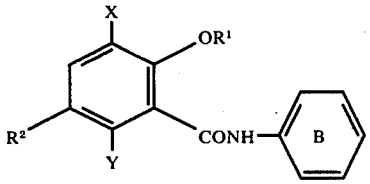

wherein $R^1$ is hydrogen, $R^2$ is cyano, X is t-butyl and ring B is phenyl substituted with at least one member of the group consisting of halogen, trifluoromethyl and cyano.

6. An anthelmintic composition comprising a salicylanilide derivative as claimed in claim 1 and an orally, parenterally or topically acceptable diluent or carrier.

7. A method of combating a liver fluke infestation in a domestic animal which comprises administering to the said animal an effective amount of a salicylanilide derivative as claimed in claim 1.

* * * * *